United States Patent
Rytky

(10) Patent No.: US 7,680,523 B2
(45) Date of Patent: Mar. 16, 2010

(54) SENSOR SYSTEM, GARMENT AND HEART RATE MONITOR

(75) Inventor: Pekka Rytky, Oulu (FI)

(73) Assignee: Polar Electro Oy, Kempele (FI)

( * ) Notice: Subject to any disclaimer, the term of this patent is extended or adjusted under 35 U.S.C. 154(b) by 884 days.

(21) Appl. No.: 11/314,746

(22) Filed: Dec. 21, 2005

(65) Prior Publication Data

US 2006/0142654 A1 Jun. 29, 2006

(30) Foreign Application Priority Data

Dec. 28, 2004 (FI) .................................. 20045503

(51) Int. Cl.
 *A61B 5/0408* (2006.01)
(52) U.S. Cl. .................. 600/388; 600/372; 600/509
(58) Field of Classification Search ......... 600/388–390, 600/393, 377, 378; 607/116
 See application file for complete search history.

(56) References Cited

U.S. PATENT DOCUMENTS

| | | | | |
|---|---|---|---|---|
| 4,517,983 A | * | 5/1985 | Toyosu et al. ............... | 600/386 |
| 4,763,660 A | | 8/1988 | Kroll et al. | |
| 4,852,571 A | * | 8/1989 | Gadsby et al. .............. | 600/396 |
| 4,957,109 A | * | 9/1990 | Groeger et al. .............. | 600/391 |
| 5,184,620 A | * | 2/1993 | Cudahy et al. .............. | 600/382 |
| 5,507,290 A | | 4/1996 | Kelly et al. | |
| 5,746,207 A | | 5/1998 | McLaughlin et al. | |
| 5,868,671 A | * | 2/1999 | Mahoney .................... | 600/382 |
| 5,938,597 A | | 8/1999 | Stratbucker | |
| 6,456,872 B1 | | 9/2002 | Faisandier | |
| 2002/0026112 A1 | | 2/2002 | Nissila et al. | |
| 2003/0092978 A1 | | 5/2003 | Fisher, III | |
| 2004/0138546 A1 | | 7/2004 | Reho et al. | |
| 2005/0010096 A1 | * | 1/2005 | Blackadar ................... | 600/388 |

FOREIGN PATENT DOCUMENTS

| | | |
|---|---|---|
| EP | 0855167 A1 | 7/1998 |
| GB | 2143135 A | 2/1985 |
| GB | 2143135 A | 2/1985 |
| JP | 2002035141 | 2/2002 |
| WO | WO 99/49934 | 10/1999 |
| WO | WO 2005/032365 A1 | 4/2005 |

* cited by examiner

*Primary Examiner*—Lee S Cohen
(74) *Attorney, Agent, or Firm*—Hoffmann & Baron, LLP

(57) ABSTRACT

The invention relates to a sensor system, a garment and a heart rate monitor. The sensor system comprises at least one flexible film structure comprising: a first insulation layer and at least one electric conductor layer formed on top of the first insulation layer and comprising an electrode area, which is configured to establish an electric contact with the surface of the user's skin and to generate as output an electric signal proportional to a momentary value of the electrocardiogram.

20 Claims, 6 Drawing Sheets

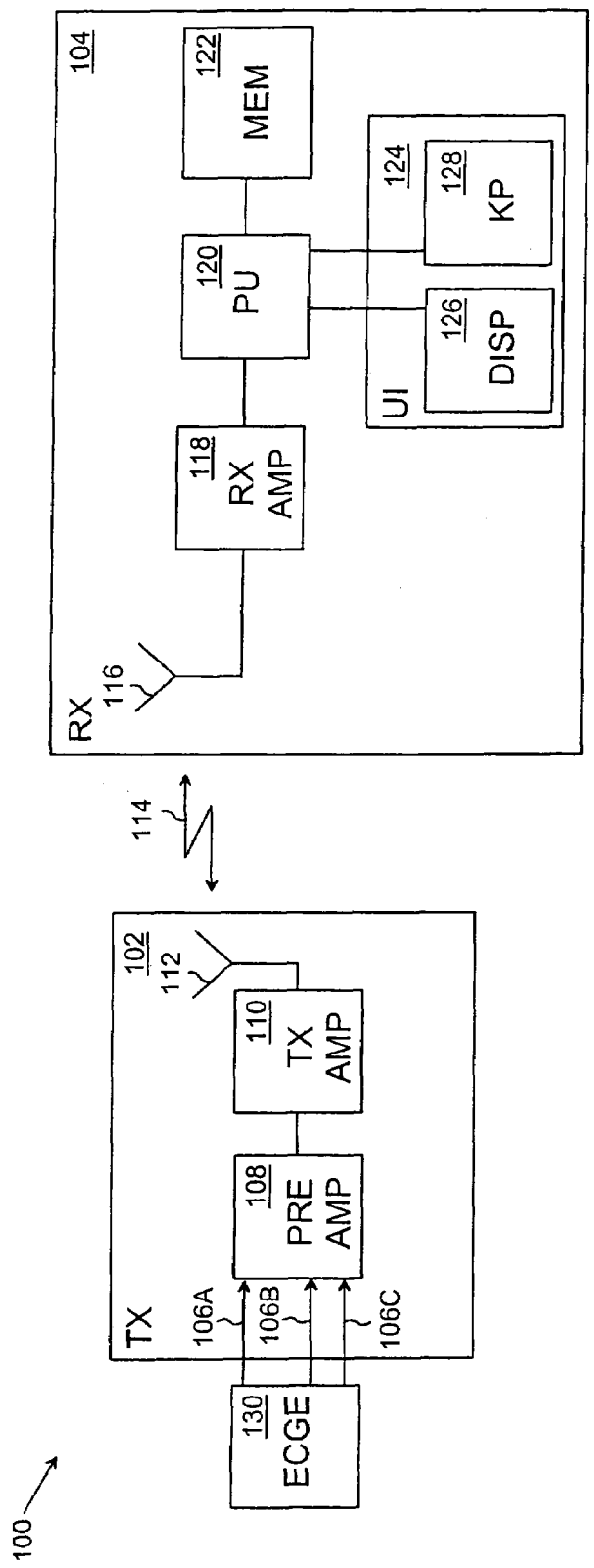
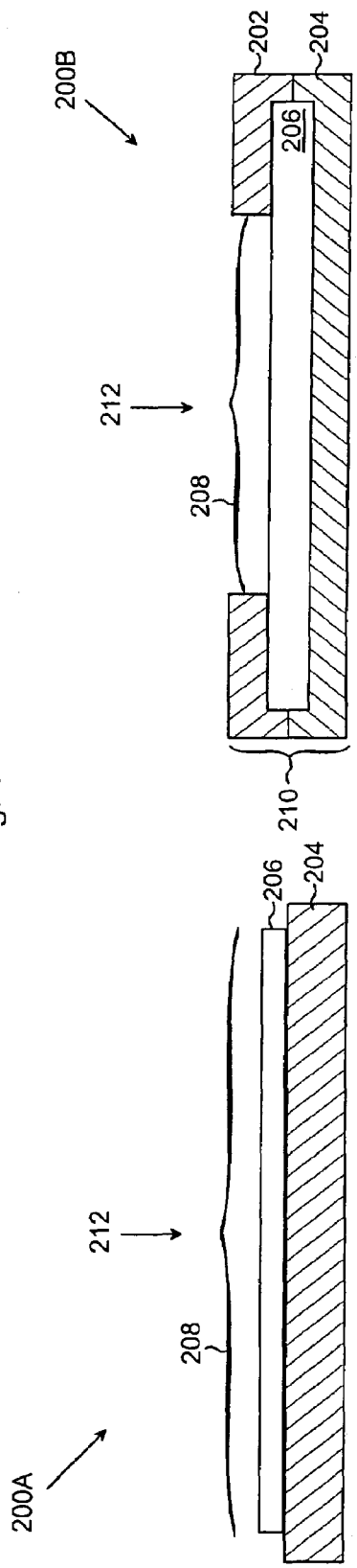
Fig. 1
Fig. 2A
Fig. 2B

SENSOR SYSTEM, GARMENT AND HEART RATE MONITOR

CROSS-REFERENCE TO RELATED APPLICATION

This application claims priority based on Finnish Patent Application No. 20045503, filed on Dec. 28, 2004, which is incorporated herein by reference.

FIELD OF THE INVENTION

The invention relates to a sensor system a garment and a heart rate monitor.

BRIEF DESCRIPTION OF THE RELATED ART

A user-specific portable heart rate monitor typically comprises a transmitter belt to be placed around the user's chest, which transmitter belt indicates an electrocardiogram from the surface of the user's skin and sends the electrocardiogram or a pulse characterizing a part thereof wirelessly to the central processing unit of the heart rate monitor, which typically is a wrist receiver to be placed on the user's wrist. When measuring an electrocardiogram weak voltage levels are determined from the surface of the skin, which requires a high-quality electric contact between the user's skin and the detection electronics of the transmitter belt. An electric contact of high quality typically requires that the transmitter belt is sufficiently tightly placed around the chest, an adequate amount of moisture between the transmitter belt and the skin to provide the tightness and a precise positioning of the transmission location within the area of the chest. The criteria presented above make the use of the heart rate monitor more difficult and increase the malfunctions of the heart rate monitor.

It is therefore useful to consider techniques that allow improving the quality of electrocardiogram measurement and facilitate the use of the heart rate monitor.

SUMMARY OF THE INVENTION

It is an object of the invention to implement a sensor system, a garment and a heart rate monitor in order to achieve a reliable heart rate measuring that in view of the user is easy to employ. A first aspect of the invention is a sensor system for indicating an electrocardiogram from the surface of the user's skin, and the sensor system is configured to be connected to a user-specific heart rate monitor and the sensor system comprises at least one flexible film structure comprising: a first insulation layer and at least one electric conductor layer formed on top of the first insulation layer and comprising an electrode area, which is configured to establish an electric contact with the surface of the user's skin and to generate as output an electric signal proportional to a momentary value of the electrocardiogram.

A second aspect of the invention is a garment comprising a sensor system integrated into the garment for indicating an electrocardiogram from the surface of the user's skin, and the sensor system is configured to be connected to a user-specific heart rate monitor and comprises at least one flexible film structure comprising: a first insulation layer and at least one electric conductor layer formed on top of the first insulation layer and comprising an electrode area, which is configured to establish an electric contact with the surface of the user's skin and to generate as output an electric signal proportional to a momentary value of the electrocardiogram.

A further aspect of the invention is a user-specific heart rate monitor comprising a sensor system for indicating an electrocardiogram from the surface of the skin, and the sensor system comprises at least one flexible film structure comprising: a first insulation layer and at least one electric conductor layer formed on top of the first insulation layer and comprising an electrode area, which is configured to establish an electric contact with the surface of the user's skin and to generate as output an electric signal proportional to a momentary value of the electrocardiogram.

The preferred embodiments of the invention are disclosed in the dependent claims.

The invention is based on the idea that a flexible film structure that may be integrated into the garment is used as the sensor of the heart rate monitor.

The sensor system, garment and heart rate monitor according to the invention provide several advantages. The flexible film structure allows implementing the sensor system such that the pressing sensation placed on the user's body remains insignificant. In addition, the use of the flexible film structure enables to decentralize the heart rate monitor so that for instance the transmitter unit typically used in heart rate monitors can be located far from the sensor system.

BRIEF DESCRIPTION OF THE DRAWINGS

In the following the invention will be described in greater detail by means of the preferred embodiments with reference to the drawings, in which FIG. 1 shows an example of the structure of a user-specific heart rate monitor;

FIG. 2A shows a cross-sectional view of a first example of a flexible film structure;

FIG. 2B shows a cross-sectional view of a second example of the flexible film structure;

DETAILED DESCRIPTION OF THE PREFERRED EMBODIMENTS

Figure 3:
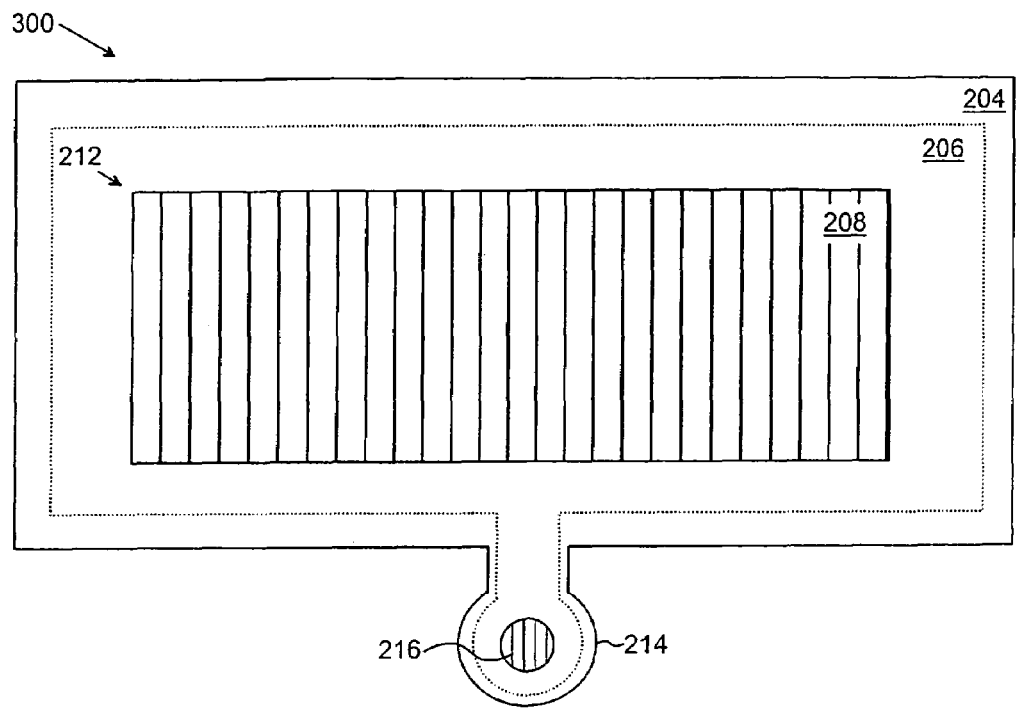
FIG. 3 shows a plan view of a first example of the flexible film structure.

FIG. 1 shows an example of the structure of a heart rate monitor 100 based on wireless data transmission. The heart rate monitor 100 typically comprises a sensor system 130, an ECG preamplifier 108 (ECG, Electrocardiogram) provided with differential input terminals, a transmitter amplifier (TX AMP) 110, a transmitter antenna 112, a receiver antenna 116, a receiver amplifier (RX AMP) 118, a processing unit (PU) 120, a memory unit (MEM) 122 and a user interface (UI) 124.

In the example shown in FIG. 1 the heart rate monitor 100 is divided into a transmitter unit 102 and a central processing unit 104 communicating through an electromagnetic field 114. However, the present solution is not restricted to the divided structure shown, instead the heart rate monitor 100 may be composed of a single functional unit, in which the functionalities of the transmitter unit 102 and the central processing unit 104 are combined.

The sensor system 130 detects the electrocardiogram of the user from the surface of the user's skin and generates as output electric signals 106A, 106B, 106C proportional to a momentary value of the user's electrocardiogram. The electric signals 106A, 106B, 106C are fed into the ECG preamplifier 108.

The ECG preamplifier 108 combines and preamplifies for instance the electric signals 106A, 106B, 106C, thus generating a preamplified ECG signal, which is fed into the transmitter amplifier 110. The transmitter amplifier 110 may include several successive amplifier levels, such as an AGC (Automatic Gain Control) amplifier and power amplifier.

An amplified ECG signal is fed into the transmitter antenna 112, which generates the electromagnetic field 114 transmitting ECG information. The ECG information may comprise for instance the electrocardiogram as such, a part thereof and/or timing information on the heart rate. The timing information may comprise a timing pulse that represents the timing of a predetermined part of the ECG.

The timing information can be determined by identifying for instance a QRS complex of the ECG and by determining the timing of the QRS complex. A QRS complex can be indicated with a pulse detector, for example. The transmitter unit 102 may for instance generate a burst that corresponds to the timing of each pulse and is sent to the central processing unit 104. The central processing unit 104 receives the bursts and may for instance determine the heart rate interval between the successive bursts.

The receiver antenna 116 indicates the electromagnetic field 114 generated by the transmitter antenna 112 and generates an induced electric signal, which is fed into the receiver amplifier 118.

The receiver amplifier 118 carries out the processing of the electric signal, such as filtering and amplification. In addition the receiver amplifier 118 may comprise several successive regulating levels.

The receiver amplifier 118 feeds the electric signal into the processing unit 120, which may perform analog signal shaping of the electric signal, such as filtering and analog-digital conversion. In addition, digital processing such as digital filtering, signal shaping, ECG signal indication and ECG signal analysis can be carried out in the processing unit 120.

The value of the heart rate variable characterizing the heart rate can be determined in the processing unit 120. The heart rate variable may be a heart rate interval, a heart rate frequency; variation in heart rate interval and/or variation in heart rate frequency.

The processing unit 120 can be implemented using analog circuits, ASIC circuits, a digital processor, memory and computer software. The processing unit 120 may form a part of the computer in the heart rate monitor 100.

Some of the data and manager information provided in the processing unit 120 can be stored in a memory unit 122 connected to the processing unit 120. In addition the memory unit 122 may comprise encoded instructions for performing the computer process in the processing unit 120.

The user interface 124 typically comprises a display unit 126 and a display controller. The display unit 126 may comprise for instance LCD (Liquid Crystal Display) components.

The user interface 124 further comprises a keypad 128 allowing the user to feed commands into the heart rate monitor 100.

The transmitter unit 102 shown in FIG. 1 typically comprises apparatus parts 106A to 112 and carries out the ECG measuring and sends the ECG information to the central processing unit 104. In some embodiments the transmitter unit 102 may comprise a heart rate indicator, which indicates a predetermined part of the electrocardiogram, generates the transmitter burst and/or the bit stream representing the timing of the predetermined part of the electrocardiogram and sends the transmitter burst to the central processing unit 104.

The central processing unit 104 typically comprises apparatus parts 116 to 128, which process the electric signal and the ECG information used in wireless data transmission and provide the user interface.

With reference to FIG. 2 let us take a closer look at the cross section of a film structure 200A of the sensor system 130. The film structure 200A comprises a first insulation layer 204 and an electric conductor layer 206 formed on top of the first insulation layer 204. The first insulation layer 204 is typically made of polycarbonate film and may function as a support structure of the film structure 200A. The electric conductor layer 206 may be made of carbon polymer paste, where carbon acts as the component conducting electricity.

The film structure 200A can also be referred to as a sensor. The sensor system 130 includes at least one film structure 200A.

FIG. 2B shows an example of an embodiment, in which a film structure 200B comprises a second insulation layer 202 such that the electric conductor layer 206 is formed between the first insulation layer 204 and the second insulation layer 202, and the second insulation layer 202 comprises an opening 212, through which opening 212 an electrode area 208 establishes an electric contact with the surface of the user's skin.

In an embodiment the first insulation layer 204 and the second insulation layer 202 are made of polycarbonate film, the thickness of which is typically fractions of millimetres. The electric conductor layer 206 can be formed for instance by pressing carbon polymer on top of the insulation layer 202, 204, where carbon functions as a conductor. Thus a thin and bendable film structure 200A, 200B is achieved, the thickness of which is fractions of millimetres and which bends in accordance with the surface of the skin. In an embodiment the thickness 210 of the film structure 200A, 200B is smaller than 0.3 millimetres. However, the solution shown is not restricted to the thickness and materials shown. The film structure shown can also be referred to as a bendable conductor base, a flex and a flexible circuit board.

In an embodiment the first insulation layer 204 is formed of a garment material such as cloth, to which the film structure 200B is fastened. Thus the garment material opening 212 may be a lead-in through the garment material, the lead-in establishing an electric contact between the electrode area 208 and the surface of the user's skin. The lead-in may be made of electrically conducting material such as polyurethane.

In an embodiment the film structure 200A, 200B includes several electric conductor layers, which are closed between the first insulation layer 204 and the second insulation layer 202. Consequently one or more insulation layers may be provided between the conductor layers. In an embodiment the electric conductor layer 206 comprises conductor structures insulated from one another. Then the conductor structures are located on the same level.

The electric conductor layer 206 comprises an electrode area 208, which establishes an electric indirect or direct contact when used on the surface of the user's skin and generates as output an electric signal 106A, 106B, 106C proportional to a momentary value of the electrocardiogram. The second insulation layer 202 comprises at least one opening 212, through which the electrode area 208 establishes an electric contact with the surface of the user's skin. Conducting material may be provided between the surface of the skin and the electrode area.

FIG. 3 shows a film structure 300 of the sensor system 130 at skin level. In this example the second insulation layer 202 forms the topmost layer, under which the electric conductor layer 206 is shown as an area defined by the dashed line. The electrode area 208 is shown through the opening 212. The first insulation layer 204 remains beneath the structure shown and it is not referred to with a reference numeral.

FIG. 3 also shows a connection structure 214 of the film structure 300, through which the electric conductor layer 206 can be connected for instance to the ECG preamplifier 108 or to any electronic equipment in the heart rate monitor. The external connection structure 214 typically comprises the film structure 200A, 200B shown in FIGS. 2A, 2B and an opening in the second insulation layer 202, through which opening the output 216 of the conductor layer can be implemented.

Figure 4A:
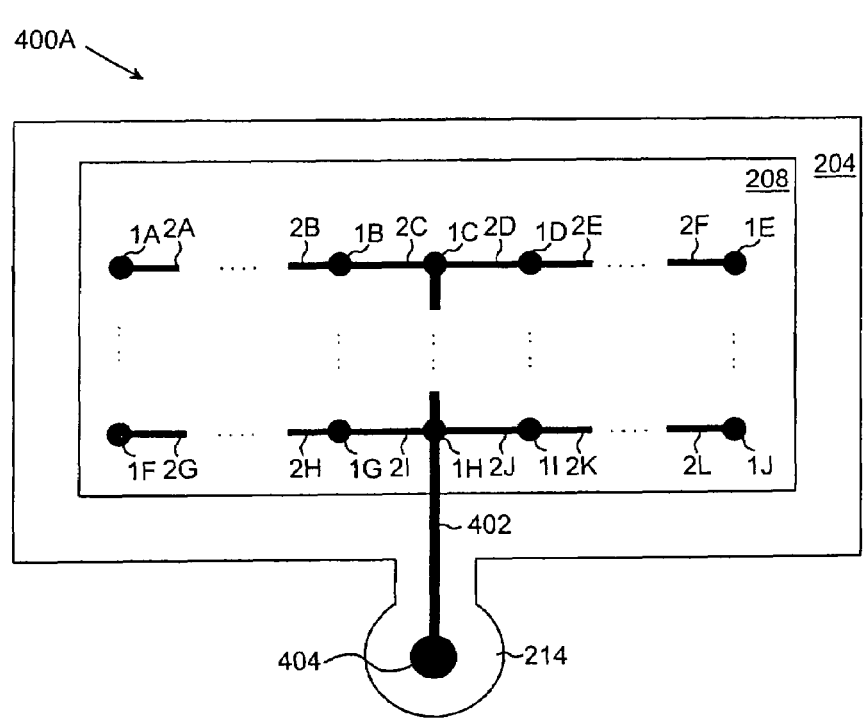
FIG. 4A shows a plan view of a second example of the flexible film structure.

In the embodiment shown in FIG. 4A the electrode area 208 of a film structure 400A comprises several electrodes 1A to 1J connected together with a first impedance connection 2A to 2L and the electrodes 1A to 1J are configured to establish an electric contact with the surface of the skin and to generate as output an electric signal proportional to the value of the electrocardiogram. The electrode area 208 is thus formed of the electrodes 1A to 1J, and the first impedance connections 2A to 2L are insulated from the user's skin.

In this context the impedance connection 2A to 2L refers to an impedance such as a resistive impedance between the electrodes 1A to 1J, whereby the resistance of the first impedance connection 2A to 2L may for example range between 1 kΩ to 1 MΩ, however, without being restricted to the values shown. The first impedance connection 2A to 2L and the desired impedance of the first impedance connection 2A to 2L can be achieved by connecting the electrodes 1A to 1J together for instance using an appropriate carbon polymer paste conductor pattern.

The electrodes 1A to 1J may form groups, in which successive electrodes are connected together in series. The electrodes 1A to 1J may also form a matrix structure, in which the electrodes 1A to 1J may be connected to three or four other electrodes 1A to, 1J. The groups can be connected to a main conductor 402, which conducts the electric signal generated by the electrodes to an electrode output 404. The use of the groups and the impedance connection between the groups allow reducing the interference signals caused by individual areas. However, the solution shown is not restricted to the electrode configuration shown, instead the electrodes 1A to 1J can be differently connected together and to the main conductor 402 depending on the embodiment.

Figure 4B:
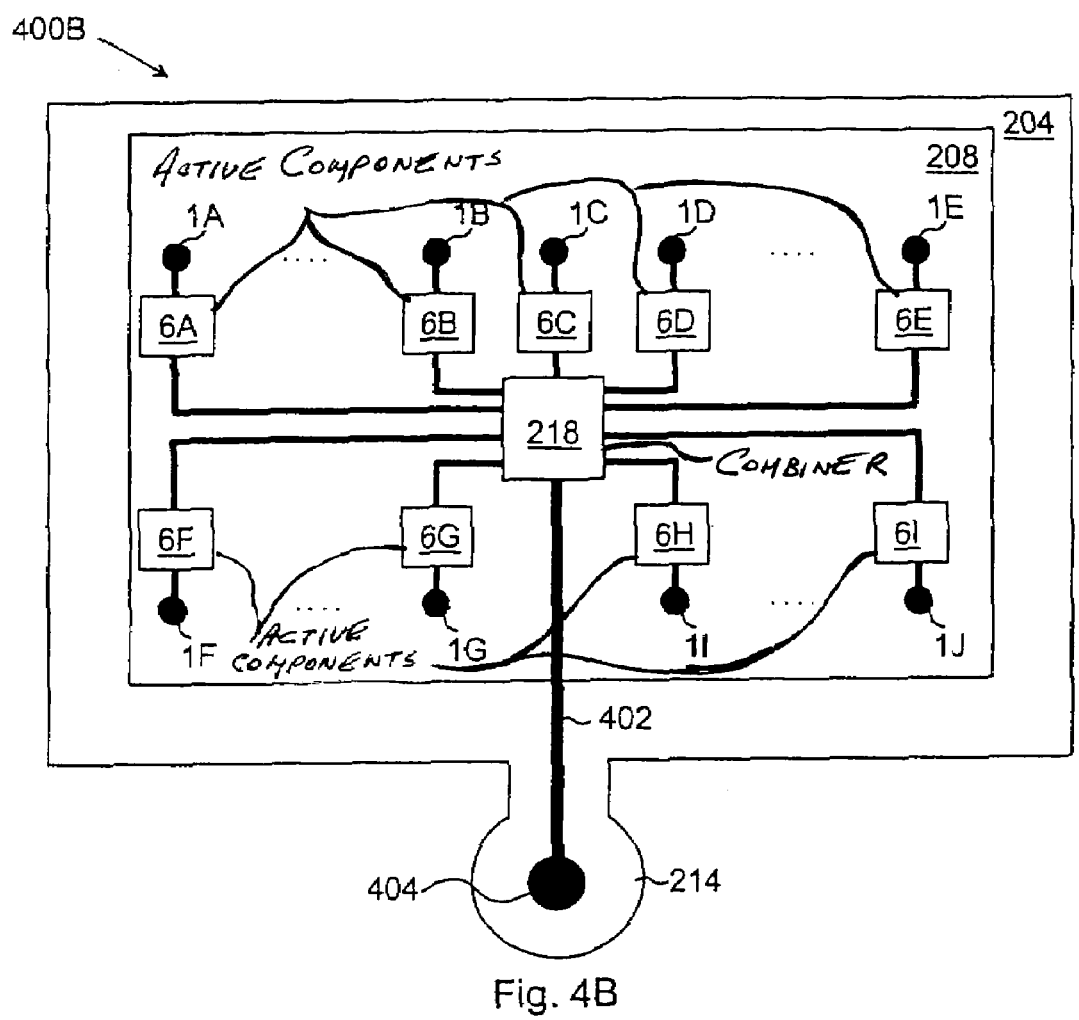
FIG. 4B shows a plan view of a third example of the flexible film structure.

In the example of the film structure 400B shown in FIG. 4B the electrodes 1A to 1J are connected to an active component 6A to 6I and the signals generated therefrom are combined in a combiner 218. The active components 6A to 6I may be amplifiers, in which case the impedance connection in FIG. 4A is manageable.

The combiner 218 may carry out a mathematical function such as a mean or a sum from the signals obtained from the active components 6A to 6I. The combiner may be an amplifier, for example. In an embodiment the combiner 218 includes a processor and is therefore able to perform advanced signal processing operations, such as selection of signals obtained from the active components 6A to 6I and/or directly from the electrodes 1A to 1J and/or determination of the correlation between the two.

Figure 5:
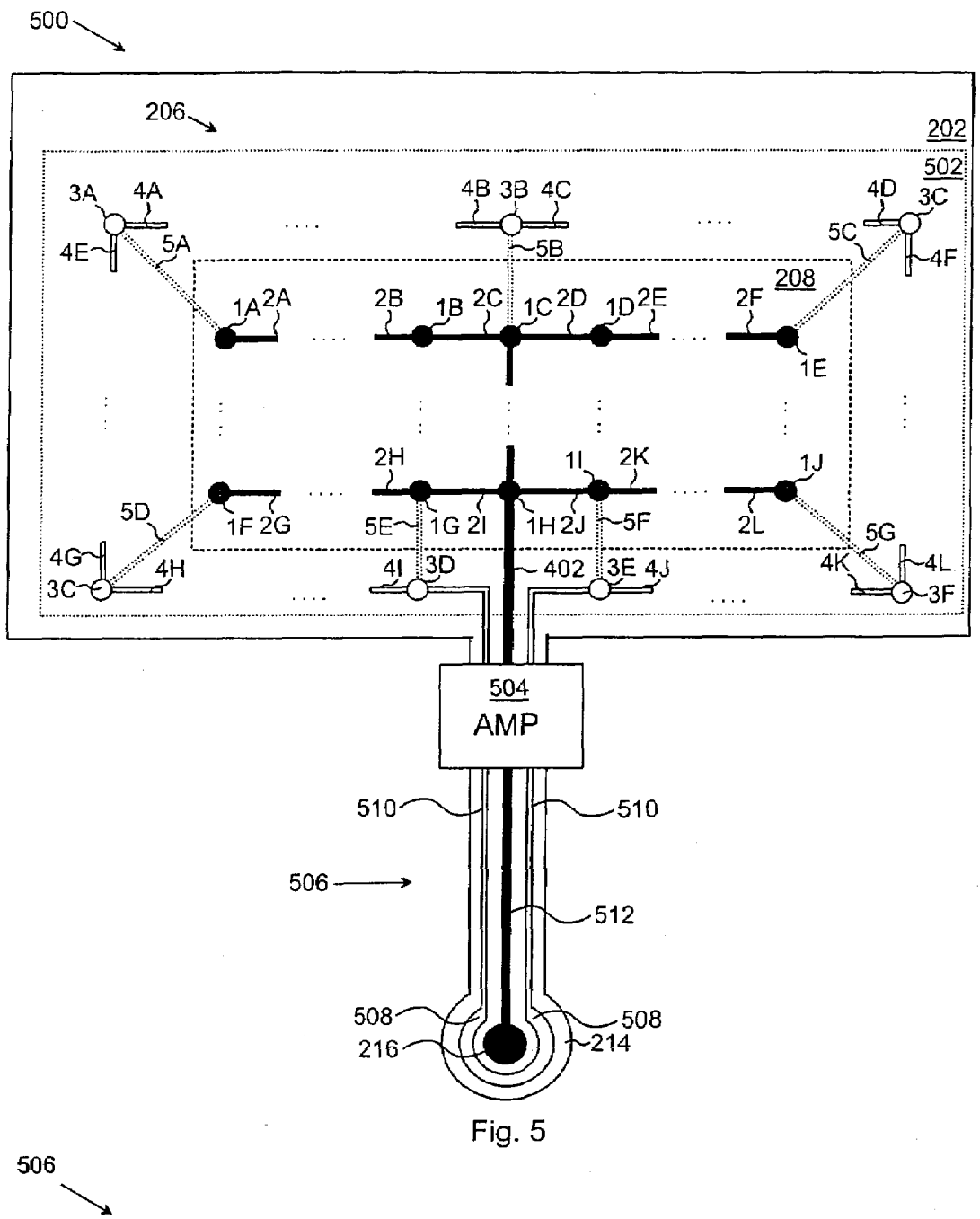
FIG. 5 shows a plan view of a fourth example of the flexible film structure.

With reference to FIG. 5, in an embodiment the electric conductor layer 206 comprises a protective area 502 surrounding the electrode area 208 at film structure 500 level. The protective area 502 is configured to establish an electric contact with the surface of the skin and to protect the sensor system 130 from static electricity. In FIG. 5 the electrode area 208 is an area defined by a dashed line and the protective area 502 is an area defined by a dashed line and a dotted line. In an embodiment the protective area 502 is separated from the electrode area 208, in which case a conductor structure corresponding to the electrode area 208 but separated from the electrode area 208 should be added to FIG. 2.

The second insulation layer 202 may comprise an opening corresponding to the opening 212 in order to establish an electric contact between the surface of the skin and the protective area 502. The electric contact may be a direct contact or an indirect one. In the latter case conducting material may be provided between the surface of the skin and the protective area 502.

The operation of the protective area 502 is based on the fact that when an induced voltage is brought from the electrode area 208 to the differential amplifier simultaneously with the voltage of the protective area 502, the static voltage component is annulled and the dependence of the output voltage of the differential amplifier on the static voltage component remains insignificant.

In an embodiment the protective area 502 comprises protective electrodes 3A to 3F connected with a second impedance connection 4A to 4L. The resistance component of the second impedance connection 4A to 4L may range for instance between 1 kΩ to 1 MΩ, however without being restricted to the values shown. The second impedance connection 4A to 4L and the desired impedance of the second impedance connection 4A to 4L can be achieved by connecting the protective electrodes 3A to 3J together using for instance an appropriate carbon polymer paste conductor pattern. The protective area 502 can be connected to the connection structure 214 with protective input conductors 510, which may be provided with an output 508 of the protective area for instance for the ECG preamplifier 108 in the heart rate monitor.

In an embodiment the protective area 502 is connected with a third impedance connection 5A to 5G to the electrode area 208, where the impedance of the third impedance connection 5A to 5G exceeds the impedance of the first impedance connection 2A to 2L. In an embodiment the resistive component of the third impedance connection exceeds 1 MΩ. In the example shown in FIG. 5 the protective electrodes 3A to 3F are connected with a third impedance connection 5A to 5G to the electrodes 1A to 1J.

The third impedance connection 5A to 5G and the desired impedance of the third impedance connection 5A to 5G can be formed for instance using an appropriate carbon polymer paste conductor pattern.

Figure 6:
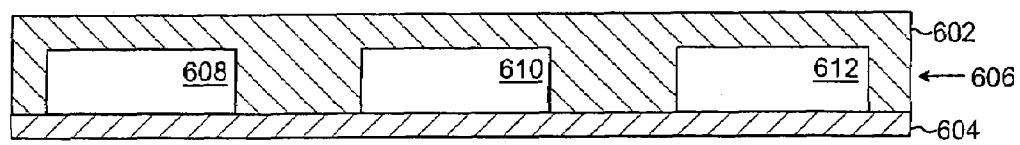
FIG. 6 shows a cross-sectional view of an example of a transfer conductor film.

With reference to FIGS. 5 and 6 the sensor system 130 comprises in one embodiment at least one transfer conductor film 506 that allows establishing an electric contact between the electric conductor layer 206 and the central processing unit 104 or between the electric conductor layer 206 and the transmitter unit 102. The transfer conductor film 506 is connected to the electric conductor layer 206 and comprises a first transfer conductor insulation layer 602 and a second transfer insulation layer 604 shown in the cross-sectional view in FIG. 6. In addition the transfer conductor film 506 comprises at least one electric transfer conductor layer 606, which is closed between the first transfer conductor insulation layer 602 and the second transfer conductor insulation layer 604. The transfer conductor layer 606 comprises at least one separated transfer input 608, 610, 612. The electric transfer conductor layer corresponds to the transfer input conductor 512 shown in FIG. 5 that functions as an extension of the main conductor 402.

The object of the transfer conductor film 506 is to function as a flexible conductor between the measuring point such as the user's chest and the electronics in the heart rate monitor such as the transmitter unit 102. In such a case the transmitter unit 102 can be freely located for instance within the area of the pelvis or within another appropriate area of the user's body, where the transmitter unit 102 can appropriately be placed.

The transfer conductor film 506 shown in FIG. 6 can also be surrounded with a conductor layer, which is surrounded with an insulation layer, in which case a coaxial structure is achieved and the interference protection of the transfer conductor film 506 is improved.

Still referring to FIG. 5, the sensor system 130 may also comprise at least one signal amplifier 504 connected to the electrode area 208 in order to amplify the electric signal generated in the electrode area 208. The signal amplifier 504 can also be connected to a protective area 502. The signal amplifier 504 is for instance a differential amplifier, the first input of which is supplied with a signal induced in the electrode area 208 and a second input is connected to the potential of the protective area 502. The signal amplifier 504 may obtain the operating voltage thereof through the transfer conductor film 506 from the transmitter unit 102 or the central unit 104, in which case the transfer conductor film 506 may be provided with a separate conductor structure for feeding power into the signal amplifier 504. The signal amplifier 504 can be placed within the sensor area or it may be connected to the transfer conductor film 506.

Instead of the signal amplifier 504 an impedance converter can be used in an embodiment when no amplification exists or when the amplification is <1.

Figure 7:
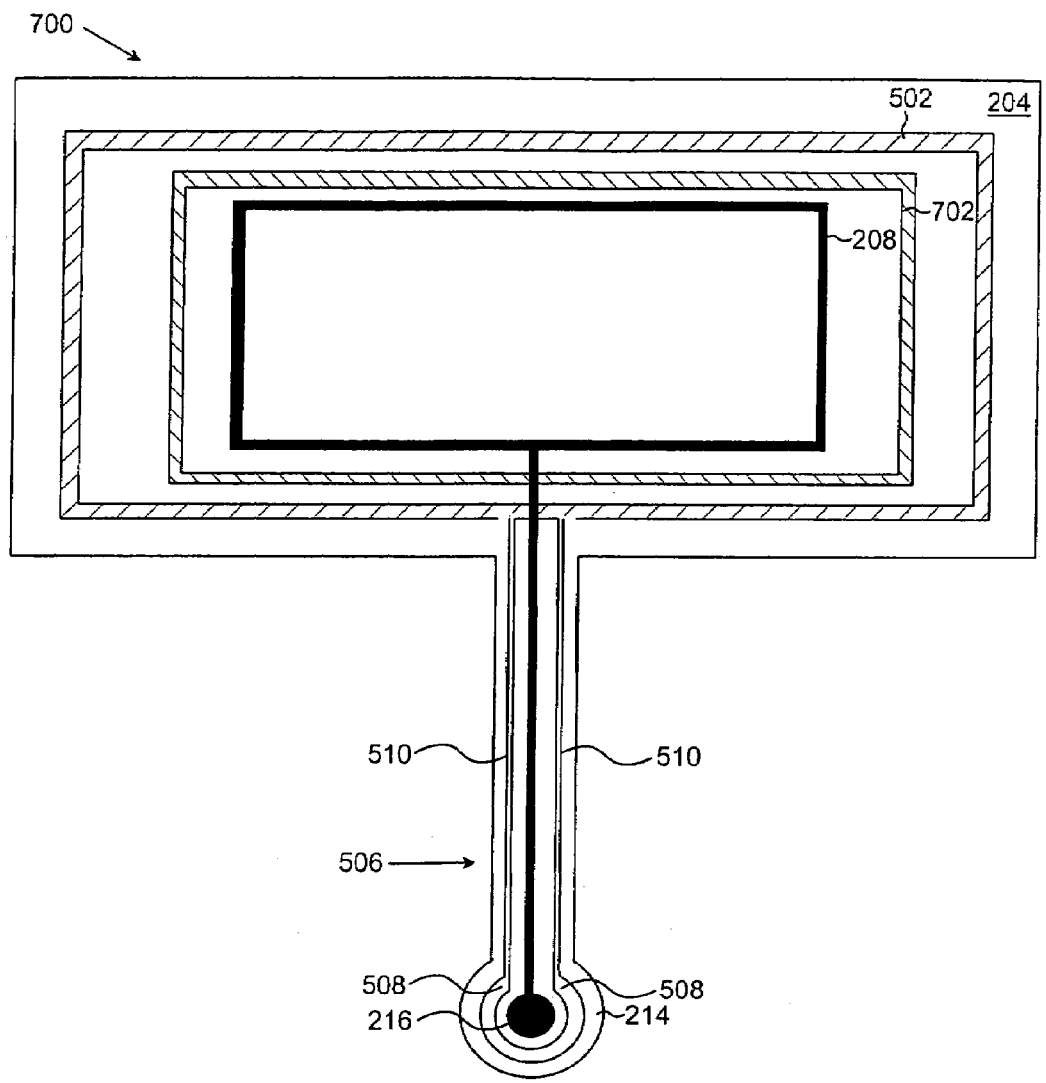
FIG. 7 shows a plan view of a fifth example of the flexible film structure.

With reference to FIG. 7 the sensor system 130 additionally comprises an insulation zone 702, which is located between the electrode area 208 and the protective area 502 at the film structure level and which is arranged to be at least partly in mechanical contact with the surface of the skin when used. The idea of the insulation layer 702 is to separate the electrode area 208 from the protective area 502 and to prevent a short circuit from occurring between the electrode area 208 and the protective area 502.

What is shown as an aspect of the invention is a garment comprising a sensor system 130 integrated into the garment for indicating an electrocardiogram from the surface of the user's skin.

Figure 8:
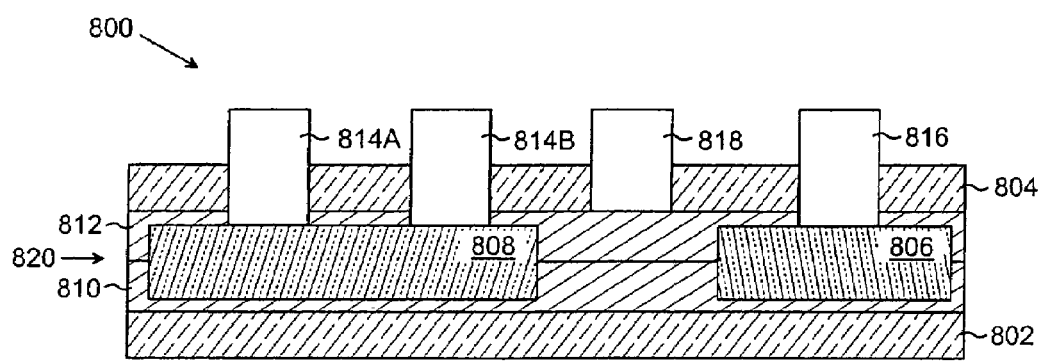
FIG. 8 shows a cross-sectional view of a second example of the flexible film structure.

FIG. 8 shows an example of a layer structure 800 comprising a first garment structure 802 and a second garment structure 804. A flexible film structure 820 according to the solution shown is provided between the first garment layer 802 and the second garment layer 804, the film structure comprising a first insulation layer 802 and a second insulation layer 804. A first electric conductor layer 806 is provided between the first insulation layer 802 and the second insulation layer 804 as well as a second electric conductor layer 808. In the example shown in the Figure the first electric conductor layer 806 functions for instance as a conductor layer for the protective area 502 and the second electric conductor layer 808 functions as the conductor layer of the electrode area 208.

In an embodiment the garment comprises at least one contact element 814A, 814B, 816 for establishing an electric contact from the electric conductor layer 806, 808 on the surface of the user's skin. The contact elements 814A, 814B shown in the Figure are contact elements of the electrode area 208, whereby the contact elements 814A, 814B may be connected for instance to the electrodes 1A to 1J shown in FIGS. 4A, 4B and 5. The contact element 816 may be connected to the protective electrode 3A to 3F shown in FIG. 5. The contact elements 814A, 814B, 816 may for instance be made of conductive polyurethane, silver-containing textile fibre and/or silver chloride plastic.

FIG. 8 also shows an insulation element 818 of the insulation area 502 that establishes a mechanical contact with the surface of the skin. The insulation element 818 may be made of electrically insulating polyurethane.

In accordance with FIG. 8 the layer structure can be made for instance by pressing the shirt from the sensor area into an injection mould, where the contact elements 814A, 814B, 818 are adhered to the conductive conductor layer 206 of the flexible film. What is then created is an integrated structure formed of the garment material and the flexible film, and a sensor system does not necessarily have to be installed separately into the body in order to use the heart rate monitor.

Figure 9:
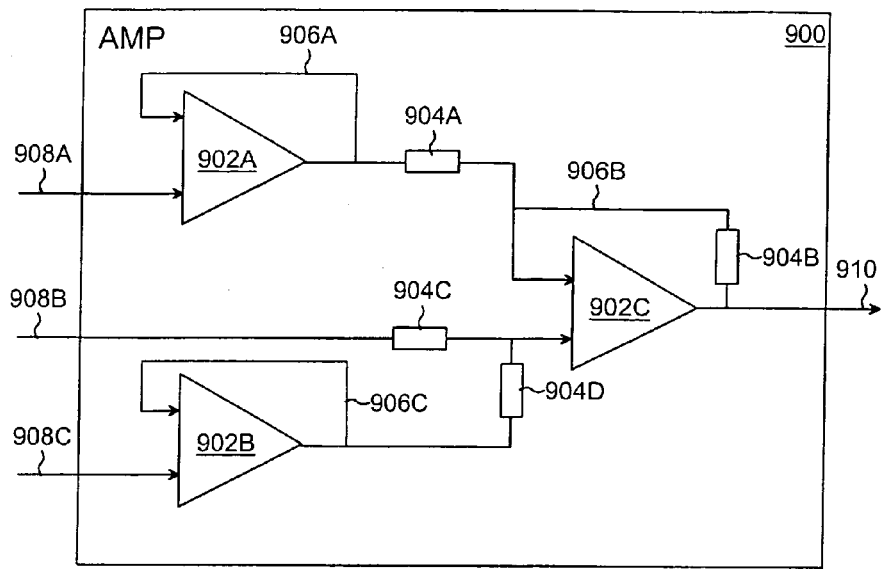
FIG. 9 shows an example of an amplifier.

FIG. 9 shows an example of a differential amplifier connection 900 that allows amplifying the signals of a sensor system 130 including two sensors. The differential amplifier connection 900 can also be referred to as an instrumentation amplifier. The differential amplifier connection 900 comprises operation amplifiers 902A, 902B, 902C provided with a feedback 906A, 906B, 906C. In the example shown the operation amplifiers 902A and 902B are voltage followers and the operation amplifier 902C is a differential amplifier. In addition the differential amplifier connection 900 comprises resistors 904A, 904B, 904C, 904D.

In the example shown the differential amplifier connection 900 comprises a first input 908A, a second input 908B and a third input 908C. The second input 908B can be connected to the potential of the protective area 502 of the sensors that may be the ground level. The second input 908B can also be connected to a separate ground electrode, which may be located anywhere on the surface of the skin. A signal obtained from the electrode area 208 of the first sensor can be fed into the first input 908A. A signal obtained from the electrode area 208 of the second sensor can be fed into the third input 908C. The differential amplifier connection 900 provides a voltage 910 proportional to the potential difference of the signals generated as output in the electrode area 208 of said two sensors.

Instead of the differential amplifier connection 900 a one-sided voltage amplifier that lacks a voltage follower 902B can be used in one embodiment. Then the signals obtained from the electrode areas 502 of different sensors are fed into the first input 908A.

Figures 10, 11:
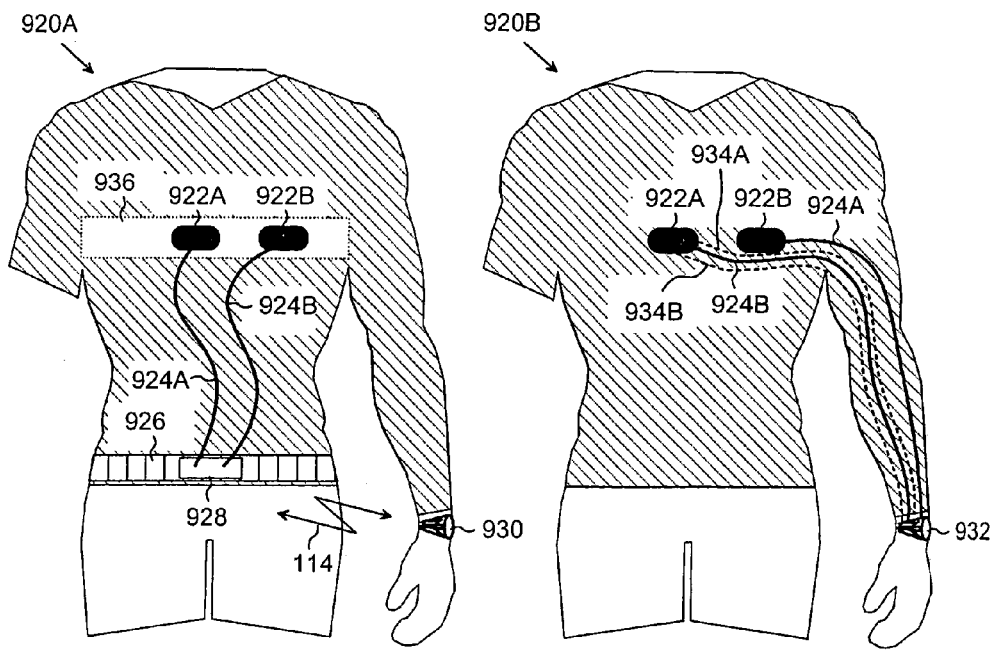
FIG. 10 shows an example of an embodiment of a garment.
FIG. 11 shows an example of a second embodiment of a garment.

Let us with reference to FIGS. 10 and 11 take a closer look at the embodiments of the sensor system 130 of the two sensors 922A, 922B. The sensor system 130 comprises the first sensor 922A and the second sensor 922B, which are implemented using the flexible film structure according to the solution shown. The sensors 922A, 922B can be connected to the amplifier 900 as shown in FIG. 9.

FIG. 10 also shows a pressing structure 936 integrated into the garment 920A. The pressing structure 936 is used to press the contact elements 814A, 814B, 816, 818 against the user's skin. The pressing structure 936 may be a flexible band structure located within the area of the sensors that places a light and broad press on the sensors 922A, 922B, whereby the flexible film structure is lightly set against the skin without causing a pressing sensation. The pressing structure 936 can also be implemented with the texture structure of the garment 920A, in which case the garment 920A is partly or completely made of flexible material. The garment may for instance be a sports shirt, a swim shirt or any garment that makes heart rate monitoring possible.

In the examples shown in FIGS. 10 and 11 the sensors 922A, 922B are integrated into a part of the shirt 920A, 920B covering the chest. The exact location of the sensors 922A, 922B in respect of the user's body is known per se.

In the embodiment shown in FIG. 10 the heart rate monitor comprises a transmitter unit 928 and a central processing unit 930 communicating through an electromagnetic field 114 or any other wireless connection. Then the electric signal induced in the sensors 922A, 922B is applied from the sensors 922A, 922B to the transmitter unit 928 for instance by means of transfer conductor films 924A, 924B. An example showing the structure of transfer conductor films 924A, 924B is shown in FIGS. 5 and 6. The transfer conductor films 924A, 924B originating from different sensors can also be integrated into the same film structure. The transmitter unit 928 can be fastened for instance to a belt 926 using a fixed fastening or snap-in fasteners such as push buttons. Then the transmitter unit 928 is located in an area, where a natural press is focused on the body, and the transmitter unit 928 does not cause any additional pressing sensation. In an embodiment the transfer conductor film 924A, 924B and the transmitter unit 928 are connected together with snap-in fasteners, which are known as such from other contexts.

If the sensors 922A, 922B include active elements 6A to 6I, 218 and/or the amplifier 504, then the operating voltage of the active elements 6A to 6I, 218 and/or the amplifier 504 can be fed from the transmitter unit 928.

In the embodiment shown in FIG. 11 the heart rate monitor comprises a central processing unit 932, which is directly connected to the sensors 922A, 922B for instance through the transfer conductor films 924A, 926B. Thus the central processing unit 932 typically comprises the preamplifier of the transmitter unit 102 shown in FIG. 1, which may be directly connected to other amplifier structures. At the same time the transmitter amplifier 110, the transmitter antenna 112, the receiver antenna 116 and the receiver amplifier 118 are not necessary.

If the sensors 922A, 922B include active elements 6A to 6I, 218 and/or the amplifier, then the operating voltage of the active elements 6A to 6I, 218 and/or the amplifier 504 can be fed from the central processing unit 932.

FIG. 11 further shows positioning means 934A, 934B for positioning the transfer conductor film 924A, 924B. The positioning means 934A, 934B can be implemented for instance with the double layer structure of the garment, in which the transfer conductor film 924A, 924B is set between the two texture layers of the garment, which are sown together at the sides thereof in such a manner that a channel is formed between the texture layers. Hooks can also be used as the positioning means 934A, 934B. In an embodiment the transfer conductor films 924A, 924B include arched forms, in which case the stretching strain placed thereon is divided equally.

Although the invention has above been described with reference to the example shown in the accompanying drawings it is apparent that the invention is not restricted thereto but can be amended in various ways within the scope of the accompanying claims.

The invention claimed is:

1. A sensor system for indicating an electrocardiogram from the surface of the user's skin, the sensor system being configured to be connected to a user-specific heart rate monitor, wherein the sensor system comprises at least one flexible film structure comprising:
   a first insulation layer; and
   at least one electric conductor layer formed on top of the first insulation layer and comprising an electrode area, the electrode area comprising electrodes configured to establish an electric contact with the surface of the user's skin and to generate as output an electric signal proportional to a momentary value of the electrocardiogram, the electrode area comprising several electrodes connected together with a first impedance connection, each of the electrodes connected together with the first impedance connection only being configurable together to establish an electric contact between all of the electrodes connected together with the first impedance connection and the surface of the skin during an application to the user's skin, the electrodes being configured to generate as output an electric signal proportional to the value of the electrocardiogram, wherein the impedance of the first impedance connection is 1 k$\Omega$ to 1 M$\Omega$.

2. The sensor system as claimed in claim 1, wherein the film structure comprises a second insulation layer such that the electric conductor layer is formed between the first insulation layer and the second insulation layer, and the second insulation layer comprises an opening, through which the electrode area establishes an electric contact with the surface of the user's skin.

3. The sensor system as claimed in claim 1, wherein the electric conductor layer further comprises a protective area surrounding the electrode area at the film structure level, the protective area being configured to establish an electric contact with the surface of the skin and to protect the sensor system from static electricity.

4. The sensor system as claimed in claim 3, wherein the protective area comprises protective electrodes connected together with a second impedance connection, the protective electrodes being configured to establish an electric contact with the surface of the skin and to protect the sensor system from static electricity.

5. The sensor system as claimed in claim 3, wherein the protective area is connected to the electrode area with a third impedance connection, where the impedance of the third impedance connection exceeds the impedance of the first impedance connection.

6. The sensor system as claimed in claim 3, wherein the sensor system also comprises an insulation zone located between the electrode area and the protective area at the film structure level and the insulation zone is arranged to be at least partly in mechanical contact with the surface of the skin when used.

7. The sensor system as claimed in claim 1, wherein the sensor system comprises:
   at least one transfer conductor film in order to establish an electric contact between the electric conductor layer and the central processing unit of the heart rate monitor or between the electric conductor layer and the transmitter unit of the heart rate monitor, and the transfer conductor film is connected to the electric conductor layer and comprises:
   a first transfer conductor insulation layer;
   a second transfer conductor insulation layer; and
   at least one electric transfer conductor layer, which is closed between the first transfer conductor insulation layer and the second transfer conductor insulation layer, and the electric transfer conductor layer comprises at least one insulated transfer input.

8. The sensor system as claimed in claim 1, wherein the sensor system further comprises at least one preamplifier connected to the electrode area in order to amplify the electric signal generated in the electrode area.

9. A garment, wherein the garment comprises a sensor system integrated into the garment for indicating an electrocardiogram from the surface of the user's skin, and the sensor system is configured to be connected to a user-specific heart rate monitor and comprises at least one flexible film structure comprising:
   a first insulation layer; and
   at least one electric conductor layer formed on top of the first insulation layer and comprising an electrode area, the electrode area comprising electrodes configured to establish an electric contact with the surface of the skin and to generate as output an electric signal proportional to a momentary value of the electrocardiogram, the electrode area comprising several electrodes connected together with a first impedance connection, each of the electrodes connected together with the first impedance connection only being configurable together to establish an electric contact between all of the electrodes connected together with the first impedance connection and the surface of the skin during an application to the user's skin, the electrodes being configured to generate as output an electric signal proportional to the value of the electrocardiogram, and at least one contact element is connected to at least one electrode, wherein the impedance of the first impedance connection is 1 k$\Omega$ to 1 M$\Omega$.

10. The garment as claimed in claim 9, wherein the garment comprises at least one contact element in order to establish an electric contact from the electric conductor layer on the surface of the user's skin.

11. The garment as claimed in claim 10, wherein, the electric conductor layer comprises a protective area surrounding the electrode area at the film structure level, the protective area being configured to establish an electric contact with the surface of the skin and to protect the sensor system from static electricity, the protective area comprising protective electrodes connected together with a second impedance connection, and the protective electrodes are configured to protect the sensor system from static electricity, and
   at least one contact element is connected to at least one protective electrode.

12. The garment as claimed in claim 9, wherein the electric conductor layer also comprises a protective area surrounding the electrode area at the film structure level, the protective area being configured to establish an electric contact with the surface of the skin and to protect the sensor system from static electricity.

13. The garment as claimed in claim 12, wherein the protective area is connected to the electrode area with a third impedance connection, where the impedance of the third impedance connection exceeds the impedance of the first impedance connection.

14. The garment as claimed in claim 12, wherein the garment further comprises an insulation zone located between the electrode area and the protective area at the film structure level and the insulation zone is arranged to be at least partly in mechanical contact with the surface of the skin when used.

15. The garment as claimed in claim 9, wherein the garment comprises a pressing structure integrated into the garment for pressing the at least one contact element against the user's skin.

16. The garment as claimed in claim 9, wherein the sensor system comprises:
   at least one transfer conductor film in order to establish an electric contact between the electric conductor layer and the central processing unit of the heart rate monitor or between the electric conductor layer and the transmitter unit of the heart rate monitor, and the transfer conductor film is connected to the electric conductor layer and comprises:
   a first transfer conductor insulation layer,
   a second transfer conductor insulation layer and
   at least one electric transfer conductor layer, which is closed between the first transfer conductor insulation layer and the second transfer conductor insulation layer, the electric transfer conductor layer comprising at least one insulated transfer input, and that the garment comprises positioning means for positioning the transfer conductor film.

17. The garment as claimed in claim 9, wherein the sensor system further comprises at least one preamplifier connected to the electrode area in order to amplify the electric signal generated in the electrode area.

18. A user-specific heart rate monitor, wherein the heart rate monitor comprises a sensor system for indicating an electrocardiogram from the surface of the user's skin, the sensor system comprising at least one flexible film structure, which comprises:
   a first insulation layer; and
   at least one electric conductor layer formed on top of the first insulation layer and comprising an electrode area, the electrode area comprising electrodes configured to establish an electric contact with the surface of the user's skin and to generate as output an electric signal proportional to a momentary value of the electrocardiogram, the electrode area comprising several electrodes connected together with a first impedance connection, each of the electrodes connected together with the first impedance connection only being configurable together to establish an electric contact between all of the electrodes connected together with the first impedance connection and the surface of the skin during an application to the user's skin, the electrodes being configured to generate as output an electric signal proportional to the value of the electrocardiogram wherein the impedance of the first impedance connection is 1 k$\Omega$ to 1 M$\Omega$.

19. The user-specific heart rate monitor as claimed in claim 18, wherein the electric conductor layer further comprises a protective area surrounding the electrode area at the film structure level, the protective area being configured to establish an electric contact with the surface of the skin and to protect the sensor system from static electricity.

20. The user-specific heart rate monitor as claimed in claim 18, wherein the user-specific heart rate monitor comprises:
   at least one transfer conductor film in order to establish an electric contact between the electric conductor layer and the central processing unit of the heart rate monitor or between the electric conductor layer and the transmitter unit of the heart rate monitor, and the transfer conductor film is connected to the electric conductor layer and comprises:
   a first transfer conductor insulation layer;
   a second transfer conductor insulation layer; and
   at least one electric transfer conductor layer, which is closed between the first transfer conductor insulation layer and the second transfer conductor insulation layer, and the electric transfer conductor layer comprises at least one insulated transfer input.

* * * * *